United States Patent
Brandt et al.

(10) Patent No.: US 11,285,272 B2
(45) Date of Patent: Mar. 29, 2022

(54) NEEDLE ASSEMBLY AND SYRINGE CONTAINING THE SAME

(71) Applicant: Terumo Europe NV, Leuven (BE)

(72) Inventors: Dirk Brandt, Woubrechtegem (BE); Geert Zephirin, Baal (BE); Luc Machiels, Nieuwerkerken (BE); Ludo Daniels, Tongeren (BE); Kurt Liesens, Tongeren (BE); Pieter Casteleyn, Herent (BE); Chris Fripon, Haasrode (BE); Jeroen Coppens, Hasselt (BE)

(73) Assignee: TERUMO EUROPE NV, Leuven (BE)

( * ) Notice: Subject to any disclaimer, the term of this patent is extended or adjusted under 35 U.S.C. 154(b) by 24 days.

(21) Appl. No.: 16/310,692

(22) PCT Filed: Jun. 15, 2017

(86) PCT No.: PCT/EP2017/064716
§ 371 (c)(1),
(2) Date: Dec. 17, 2018

(87) PCT Pub. No.: WO2017/216315
PCT Pub. Date: Dec. 21, 2017

(65) Prior Publication Data
US 2019/0247590 A1    Aug. 15, 2019

(30) Foreign Application Priority Data
Jun. 17, 2016   (EP) ..................... 16175067

(51) Int. Cl.
*A61M 5/34*    (2006.01)

(52) U.S. Cl.
CPC ............ *A61M 5/346* (2013.01); *A61M 5/343* (2013.01); *A61M 2205/0244* (2013.01); *A61M 2207/10* (2013.01)

(58) Field of Classification Search
CPC ...... A61M 5/343; A61M 5/346; A61M 5/329; A61M 5/34
See application file for complete search history.

(56) References Cited

U.S. PATENT DOCUMENTS

| 3,470,604 A | * | 10/1969 | Zenick | ................ B29C 66/5344 |
| | | | | 29/447 |
| 2016/0184532 A1 | * | 6/2016 | Ooyauchi | ............. A61M 5/158 |
| | | | | 604/239 |

FOREIGN PATENT DOCUMENTS

| EP | 2979717 A1 | 2/2016 |
| WO | WO01/91826 A2 | 12/2001 |

(Continued)

OTHER PUBLICATIONS

International Search Report and Written Opinion for PCT Patent App. No. PCT/EP2017/064716 (dated Sep. 25, 2017).

*Primary Examiner* — Emily L Schmidt
(74) *Attorney, Agent, or Firm* — Kenealy Vaidya LLP

(57) ABSTRACT

Some embodiments are directed to a needle assembly that includes a needle having a textured portion and non-textured portion adjacent to the textured portion, and a hub arranged over at least a part of the textured portion of the needle.
The textured portion includes laser etched grooves formed on an outer surface of the needle and oriented in a circumferential direction of the needle. Each of the laser etched grooves has two protruded portions and a dented portion interposed between the two protruded portions.
Each of the two protruded portions has a top surface located above an outer surface of non-textured portion, and the dented portion has a bottom surface located below the outer surface of non-textured portion.

13 Claims, 3 Drawing Sheets

(56) References Cited

FOREIGN PATENT DOCUMENTS

WO    WO 2015/037233    *   3/2015    .............. A61M 5/32
WO    WO2015/037233 A1    3/2015

* cited by examiner

NEEDLE ASSEMBLY AND SYRINGE CONTAINING THE SAME

CROSS REFERENCE TO RELATED APPLICATIONS

This application is a national phase filing under 35 C.F.R. § 371 of and claims priority to PCT Patent Application No. PCT/EP2017/064716, filed on Jun. 15, 2017, which claims the priority benefit under 35 U.S.C. § 119 of European Patent Application No. 16175067.4, filed on Jun. 17, 2016, the contents of each of which are hereby incorporated in their entireties by reference

BACKGROUND

The presently disclosed subject matter relates to a needle assembly including a needle and a hub partially arranged or molded over the needle. In particular, the presently disclosed subject matter relates to a needle assembly when the needle shall resist to a minimum extracting or pulling force applied between the hub and the needle. Such resistance to an extracting or pulling force will be hereafter discussed as the bonding strength, as the hub is molded over a part of the needle.

Document WO2014155481A1 describes a needle assembly. However, for specific uses or specific customers, the bonding strength might need to be further increased.

SUMMARY

The presently disclosed subject matter aims to address the above mentioned drawbacks of the related art, and to propose first a needle assembly having an increased bonding strength, while the costs, the complexity of the components and of the manufacturing process shall not be increased.

In this aim, a first aspect of the presently disclosed subject matter is a needle assembly including a needle having a textured portion and non-textured portion adjacent to the textured portion, and
a hub arranged over at least a part of the textured portion of the needle, characterized in that the textured portion includes laser etched grooves formed on an outer surface of the needle and oriented in a circumferential direction of the needle, wherein each of the laser etched grooves has two protruded portions and a dented portion interposed between the two protruded portions so as to form an anchorage with the hub arranged over at least a part of the textured portion, wherein each of the two protruded portions has a top surface located above an outer surface of non-textured portion and the dented portion has a bottom surface located below the outer surface of non-textured portion. The bonding strength of the assembly is improved by the grooves oriented along a circumferential direction (in other words, the grooves are transverse to an axial direction of the needle) and the protruded portions, which create an efficient anchorage between the needle and the hub. In addition, the grooves are laser etched, and this process creates less particles and/or dust than sand blasting does. Still another advantage from the laser etching is that the protruded portions (or lateral protrusions) are automatically or simultaneously manufactured during the etching of the grooves, as the laser beam melts material to etch the grooves, and this melted material is simultaneously pushed outwards or sideward, thereby creating the protruded portions. The protruded portions are directly adjacent to the grooves' lateral walls, and/or are formed in continuity to the grooves' walls. One should note that laser etched grooves are designating grooves engraved or formed in the material of the needle or cannula by a laser beam. In other words, the hub covers some of the circumferential grooves and this creates an efficient bonding with the hub's material.

Alternatively, the presently disclosed subject matter relates to a needle assembly including a needle having a textured portion and non-textured portion adjacent to the textured portion, and a hub arranged over at least a part of the textured portion of the needle,
characterized in that the textured portion includes laser etched grooves formed on an outer surface of the needle and oriented in a circumferential direction of the needle, wherein each of the laser etched grooves has two protruded portions and a dented portion interposed between the two protruded portions, the dented portion of the laser etched grooves covered by the hub being filled with a material constituting the hub, and wherein each of the two protruded portions has a top surface located above an outer surface of non-textured portion and the dented portion has a bottom surface located below the outer surface of non-textured portion.

The circumferential or transverse grooves do not form any thread, they are simply oriented perpendicularly to the axial direction of the needle. They can be easily manufactured by a laser beam having a relative movement with the needle in the transverse direction, so that a plurality of needles can be etched in one go. The transverse direction is perpendicular to the needle axis, and might be in the range of 90°±10°.

Advantageously, the protruded portions are present all along the laser etched grooves.

Advantageously, the hub is arranged over the entire textured portion. This embodiment provides an improved resistance to the assembly, as the transverse or circumferential laser etched grooves might affect the bending resistance of the needle, but the hub arranged over the entire textured portion provides the desired bending resistance.

Advantageously, the laser etched grooves are separated by a given pitch, the given pitch being lower than a predetermined value, so that protruded portions of two adjacent laser etched grooves have at least a common portion or overlap. The applicant has noticed that below a predetermined pitch, the lateral portions or protrusions of two adjacent grooves present a common portion, thereby increasing the resistance of the bonding joint.

Advantageously, the given pitch is lower than the width of a single laser etched groove and its two protruded portions. The Applicant noticed that such given pitch ensures that the lateral protrusions of two adjacent grooves will join each other so as to form a common portion. The width of a single groove and its two lateral protrusions can be easily determined by etching a specific needle with one groove.

Advantageously, the given pitch is chosen so that the common portion is lower than the height of the protruded portions.

Advantageously, the given pitch is chosen so that there is an indent arranged on a top portion between two protruded portions having at least a common portion or overlap. Such indent increases the bonding strength, as the indent creates a further anchorage with the hub's material.

Advantageously, the laser etched grooves have a minimum depth of 10 μm below the outer surface of non-textured portion for a needle having a textured area covered by the hub of at least 3 mm length along the needle axial direction. For a 23 G needle, this embodiment provides a bonding strength well above 34 Newton. It is to be noted that the grooves do not need to have a uniform and/or constant depth. It is enough to have, in the transverse direction, an angular sector of the groove having the desired depth. For instance, if the laser etched grooves are deeper than the minimum depth along a 30° sector for one side (180°) of the needle, the bonding strength will be ensured. In other words, the minimum depth of the laser etched grooves may possibly be satisfied at least along 16% of the circumference of the needle. In other words, the depth of the laser etched grooves does not need to be constant, and might even be lower than the minimum depth in limited portions of the grooves, the anchorage still satisfying the desired bonging strength (i.e. axial resistance of the assembly).

In one embodiment, the minimum depth is 15 μm or more.

Advantageously, the minimum depth is below 15 μm for a 18 G needle, below 40 μm for a 23 G needle, and below 17 μm for a 32.5 G needle.

Advantageously, the dented portion of the laser etched grooves has a minimum depth, the needle presents a wall thickness, and the minimum depth is chosen in the range from 10% to 50% of the wall thickness. This embodiment provides a correct bonding strength, while the remaining wall thickness is from 90% to 50% of the initial wall thickness, thereby ensuring the absence of a hole in the wall thickness avoiding any plastic material flow into the central channel.

Advantageously, the protruded portions have a minimum height of 10 μm above the outer surface of non-textured portion.

In one embodiment, the minimum height is 20 μm or more.

Advantageously, the pitch is 125 μm±40 μm.

In one embodiment, the pitch is 125 μm±25 μm.

Alternatively, the pitch may be from 100 to 250 μm, for example 150 μm, 175 μm or 217 μm, ±40 μm.

Advantageously, the textured area covered by the material of the hub presents a minimum length of 3 mm along the longitudinal direction of the needle.

More specifically, for a 18 G needle, the minimum height is 4 μm above the outer surface of non-textured portion and the minimum depth is 7 μm for a textured portion length of 2 mm.

Advantageously, the hub is molded over the needle, or is heat-deformed over the needle, and is manufactured with a molding material chosen from polymers, and containing at least one of polyethylene, polypropylene, or cyclic polyolefin.

Advantageously, the laser etched grooves extend in the circumferential direction along 360°.

Advantageously, the laser etched grooves extend in the circumferential direction along about or less than 180°.

Advantageously, the laser etched grooves are shifted between two opposite sides of the needle.

A second aspect of the presently disclosed subject matter relates to a syringe including a needle assembly according to the first aspect of the presently disclosed subject matter.

BRIEF DESCRIPTION OF THE FIGURES

Other features and advantages of the presently disclosed subject matter will appear more clearly from the following detailed description of particular non-limitative examples of the presently disclosed subject matter, illustrated by the appended drawings wherein.

DETAILED DESCRIPTION OF EXEMPLARY EMBODIMENTS

Figure 1:
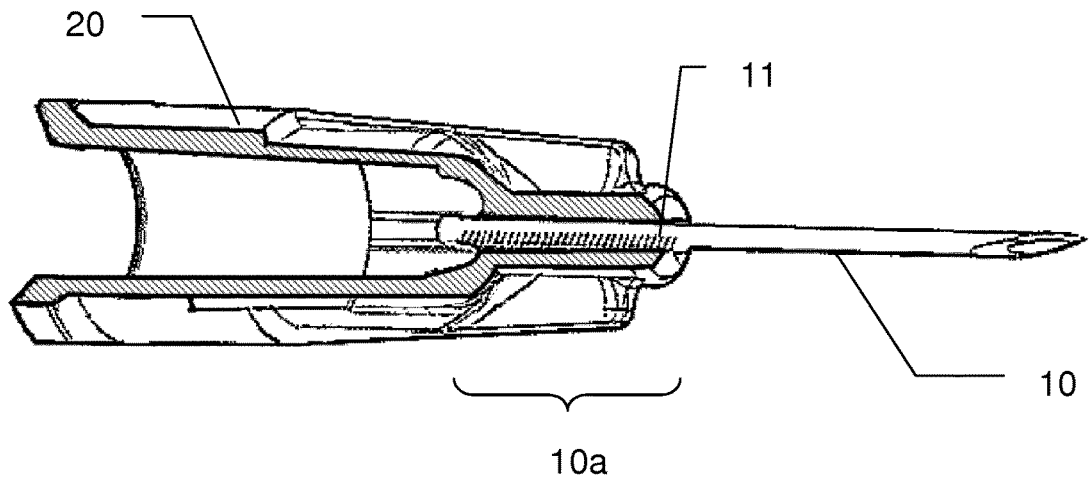
FIG. 1 represents a general view of a needle assembly according to the presently disclosed subject matter, including a hub molded over a proximal portion of a needle.

FIG. 1 is a general view of a needle assembly including a hub 20 molded over a proximal end 10a of a needle 10. Typically, the hub 20 is coupled to a syringe for injecting a liquid into a patient's body.

Depending on the liquid to be injected and in particular on its viscosity, pressure forces created during injection apply an extraction force onto the needle. Combined to mechanical forces which might be directly applied to the needle, it may be necessary for the assembly to withstand these combined mechanical forces, and the joint between the needle 10 and the hub 20 must or should present a minimum bonding strength. For example, it might be required for a 23 G needle assembly to resist a minimum pull or extract force of 34 N applied longitudinally between the hub 20 and the needle 10.

As the hub is molded over the proximal end 10a of the needle 10, the bonding strength depends on several factors, and in particular, the bonding strength highly depends on the geometry of the needle 10. An aspect of the presently disclosed subject matter relates to a succession or a series of laser etched grooves 11, creating a textured area implemented on the outer surface of the needle 10, as can be seen in FIG. 1.

Figure 2:
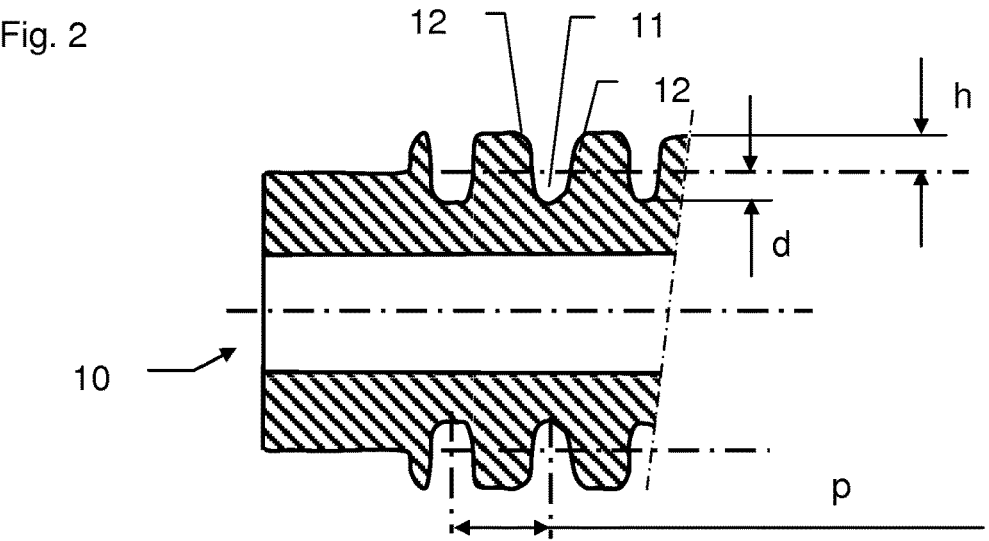
FIG. 2 represents a partial longitudinal cross section of the proximal portion of an embodiment of the needle of FIG. 1.
Figure 3:
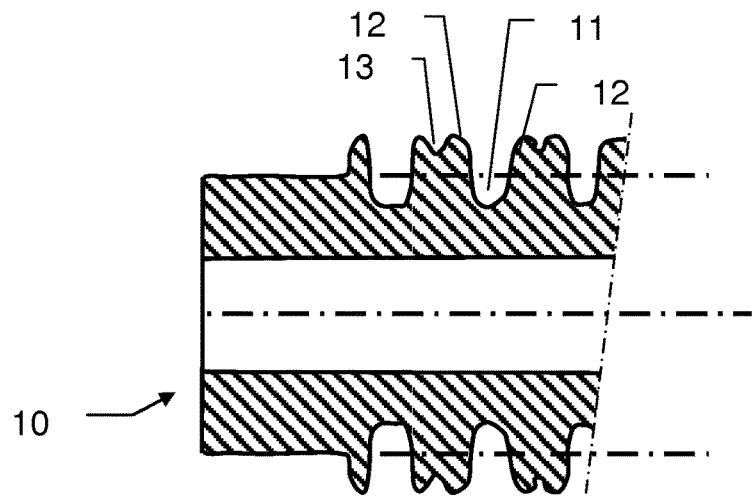
FIG. 3 represents a partial longitudinal cross-section of the proximal portion of another embodiment of the needle of FIG. 1.

FIG. 2 and FIG. 3 are partial longitudinal cross-sections of possible embodiments of the succession of laser etched grooves 11 according to the presently disclosed subject matter.

FIG. 2 represents an embodiment of the succession of laser etched grooves 11, separated by a pitch p. In other words, the laser etched grooves 11 are regularly spaced from each other, and the distance between the laser etched grooves 11 is the pitch p. Each laser etched groove 11 presents two protruded portions 12 and is oriented along the transverse direction of the needle 10. In other words, the laser etched grooves 11 are perpendicular to the longitudinal axis of the needle 10, and in particular, they do not form a thread and/or are not arranged to form any helix. The laser etched grooves 11 present a depth d measured from the initial outer surface of the needle 10, to the bottom surface of the laser etched grooves 11.

The laser etched grooves 11 are laser etched, so that the protruded portions 12 are formed simultaneously to the texturing (laser etching) of the laser etched grooves 11. Consequently, the protruded portions 12 are automatically formed, so that there is no specific or additional process step to obtain such protrusions. The protruded portions 12 present a height h measured from the initial outer surface of the needle 10, to the top surface of the protruded portions 12.

FIG. 3 represents another embodiment of the succession of laser etched grooves 11. In this other embodiment, one can notice the presence of an indent 13 located on the top portion of each protruded portion 12 separating two laser etched grooves 11. This is a difference in this other embodiment compared to the previous embodiment.

Figure 4:
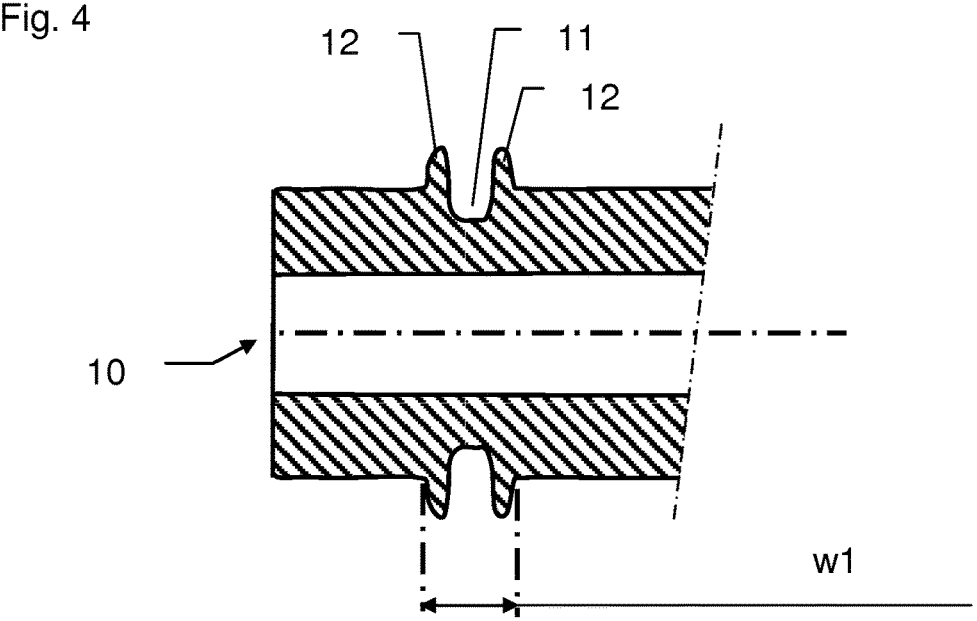
FIG. 4 represents a single laser etched groove on a needle.

FIG. 4 represents a single laser etched groove 11, arranged on the outer surface of a needle 10. Similarly, to the previous embodiments, the laser etched groove 11 presents two protruded portions 12, formed by the laser etching process. The width of this single laser etched groove 11 is w1.

Reverting to FIGS. 2 and 3, one can notice that the protruded portions 12 of two adjacent laser etched grooves 11 are wider than the protruded portions 12 of the single laser etched groove 11 of FIG. 4. This is because the protruded portions 12 of FIGS. 2 and 3 overlap and/or present a common portion, because the pitch p is shorter or smaller than the width w1 of the single laser etched groove 11. Consequently, the protruded portions 12 of FIGS. 2 and 3 present a higher resistance to an axial stress created by an axial pulling force, as the protruded portions 12 have a larger root or width with the core material of the needle.

Reverting to the embodiment of FIG. 3, the indent 13 is present because the protruded portions 12 of two adjacent laser etched grooves 11 present a common portion smaller than the height of the protruded portions 12. This is the result either of a longer pitch p than the one of FIG. 2, or of a smaller depth of the laser etched grooves 11 (as there is less molten material to generate the protruded portions 12). The presence of the indent 13 increases the resistance to the axial stress.

It is to be noted that the presently disclosed subject matter covers the possibility of a succession of single laser etched grooves 11 of FIG. 4 spaced by a longer pitch, so that the protruded portions 12 will not overlap and/or will not present any common portion.

Figure 5:
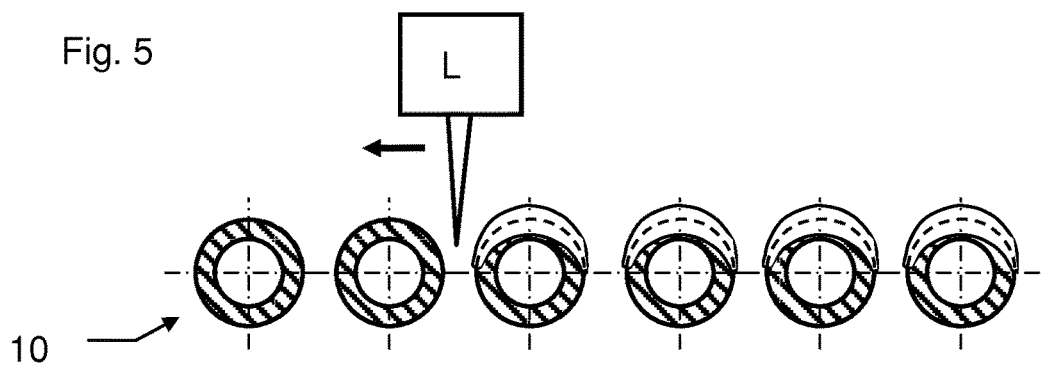
FIG. 5 represents a laser etching head during a laser etching process of a plurality of needles of FIG. 2, 3 or 4.

FIG. 5 represents an example of a manufacturing process to obtain the laser etched grooves 11 of FIG. 2, 3 or 4. A laser head L is located above a plurality of needles 10, and a relative horizontal movement is applied between the laser head L and the needles 10, so that laser etched grooves 11 and the protruded portions 12 are created on the outer surface of the needles 10. To obtain laser etched grooves 11 having a depth greater than what may be required, it might be necessary to perform several times the same displacement. A number of 5 passes, 7 passes or 10 passes might be necessary, for example.

After one side of the needles 10 is engraved, the other side can be exposed to the laser etching. It might be encompassed to shift or offset the needles so as to obtain the grooves of the two opposite sides offset or shifted, to increase the torque resistance.

As an example, one can use a laser source (Nd:YVO4) having a power between 1.2 kW-1.7 kW, pulse frequency between 60 kHz and 85 kHz, focal lens of 100 mm, a spot size of 25 µm-30 µm to engrave at a relative speed between 500 mm/s to 2500 mm/s needles such as 23 G needles (7 passes at 800 mm/s) or 32.5 G needles (10 passes at 2000 mm/s).

Figure 6:
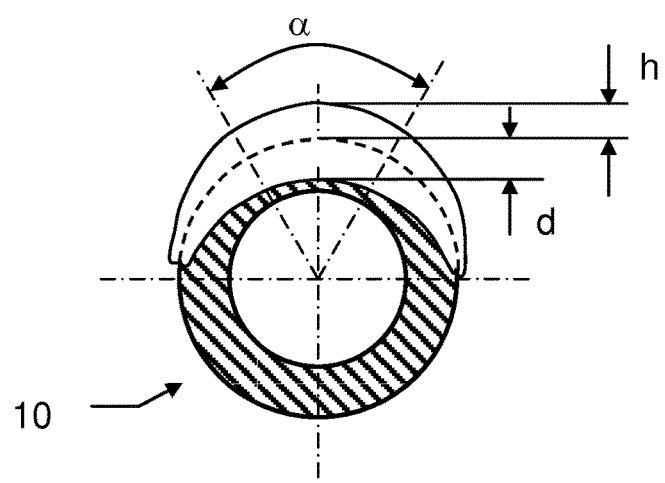
FIG. 6 represents a transverse cross-section of the needle of FIG. 2, 3 or 4.

FIG. 6 represents a cross-section of a needle 10 of FIG. 2, 3 or 4. Since the manufacturing process of FIG. 5 uses a laser head L having a horizontal relative movement with respect to the needles 10, the depth d of the laser etched grooves 11 and the height h of the protruded portions 12 are not constant all along the circumference of the needle 10.

Indeed, the laser beam is more efficient in an upper angular portion α, and the depth d of the laser etched grooves 11 is maximum in the upper angular portion α. The same holds for the height h of the protruded portions 12.

The Applicant noticed that since the depth d was greater than what may be required (10 µm for example if the grooves form an area of at least 3 mm along the needle's axis) in the angular portion α, then the minimum bonding strength can still be achieved. The angular portion α is at least 30°. In one embodiment, the angular portion α is at least 45°.

Comparative Testing

Comparative testing has been conducted to check the bonding strength of hub-needle joints. 18 G, 23 G and 32.5 G needles assemblies with the laser etched grooves 11 according to the presently disclosed subject matter were tested, and compared with baseline needles without any texturation and with needles with a sandblasted or microblasted area (roughness Ra of 4.5 µm).

All samples were over-molded with polypropylene (Grade: Total PPM H350) and then tested to check the force that may be required to pull the needle out of the hub at a speed of 50 mm/min (referred to as "bonding strength").

These bonding tests have been performed according to the method of ISO standard NBN EN ISO 7864-2016.

This standard further provides the minimum bonding strength according to the diameter of the needle as follows:

| Needle diameter (gauge) | Minimum bonding strength (Newton) |
| --- | --- |
| 18 | 69 |
| 23 | 34 |
| 32.5 | 11 |

The table below summarizes the results for the bonding tests of 18 G, 23 G and 32.5 G needles texturized according to the presently disclosed subject matter (in bold) in view of related-art solutions and twenty samples were used for each type of tested needle assembly.

| Needle | depth d (µm) | height h (µm) | Pitch p (µm) | Textured length (mm) | Bonding strength (N) | Spec. (N) |
| --- | --- | --- | --- | --- | --- | --- |
| 18G Laser etched | 5 | 15 | 100 | 4 | 127 | 69 |
| 18G Laser etched | 40 | 30 | 100 | 4 | 128 | 69 |
| 18G/no treatment | — | — | — | — | 9 | 69 |
| 23G Laser etched | 50 | 44 | 100 | 3 | 147 | 34 |
| 23G Laser etched | 34.5 | 17.4 | 125 | 3 | 142 | 34 |
| 23G Laser etched | 28 | 24 | 150 | 3 | 130 | 34 |
| 23G/no treatment | — | — | — | — | 7.5 | 34 |
| 23G Sand blasting (Ra 4.5 µm) | — | — | — | 4 | 13.9 | 34 |
| 32.5G laser etched | 17.2 | 14.4 | 125 | 3 | 21.9 | 11 |
| 32.5G/no treatment | — | — | — | — | 3 | 11 |
| 32.5G Sand blasting (Ra 4.5 µm) | — | — | — | 4 | 5 | 11 |

From the above table, the laser etched configurations exhibit a bonding strength well above what the ISO may require of respectively 69 N, 34 N or 11 N for the 18 G, 23 G or 32.5 G needles, with a 3 or 4 mm long textured area.

18 G needle assemblies without any texture or treatment on the needles show a bonding strength of 9 N, which is below 69 N.

Similarly, 23 G needles assemblies without any treatment exhibit a bonding strength of 7.25 N, which is clearly below 34 N. The same holds for the 32.5 G needles without any treatment: the bonding strength is 3 N, with a minimum strength of 11 N.

The micro-blasted (sandblasted) needles do not pass the test either, with bonding strengths just slightly higher than the bonding strengths obtained with the needles without any treatment.

It is possible to conclude that a succession of transverse laser etched grooves significantly improves the bonding strength when compared to related-art solutions.

Testing of Different Textured Portions

Further from the above tests, different dimensions have been investigated, namely different heights h of the protruded portion, different depths d of the laser etched grooves and different lengths of the textured portion.

The below table summarizes the dimensions of the tested needles.

| Needle diameter | outside diameter (mm) | | inside diameter (mm) | |
|---|---|---|---|---|
| (Gauge) | min | max | min | max |
| 18 | 1.23 | 1.27 | 0.91 | 0.98 |
| 23 | 0.63 | 0.648 | 0.38 | 0.43 |
| 32.5 | 0.217 | 0.228 | 0.117 | 0.148 |

18 G Needles

Polypropylene needle hubs were over-molded on a textured needle according to the presently disclosed subject matter and various value of depth (d), height (h) and textured length. Pitch of the texture portion was 125 μm. These needle assemblies were then evaluated according to the ISO standard 7864-2016, five needle assemblies were evaluated for each set of values (depth, height, textured portion length).

Figure 7:
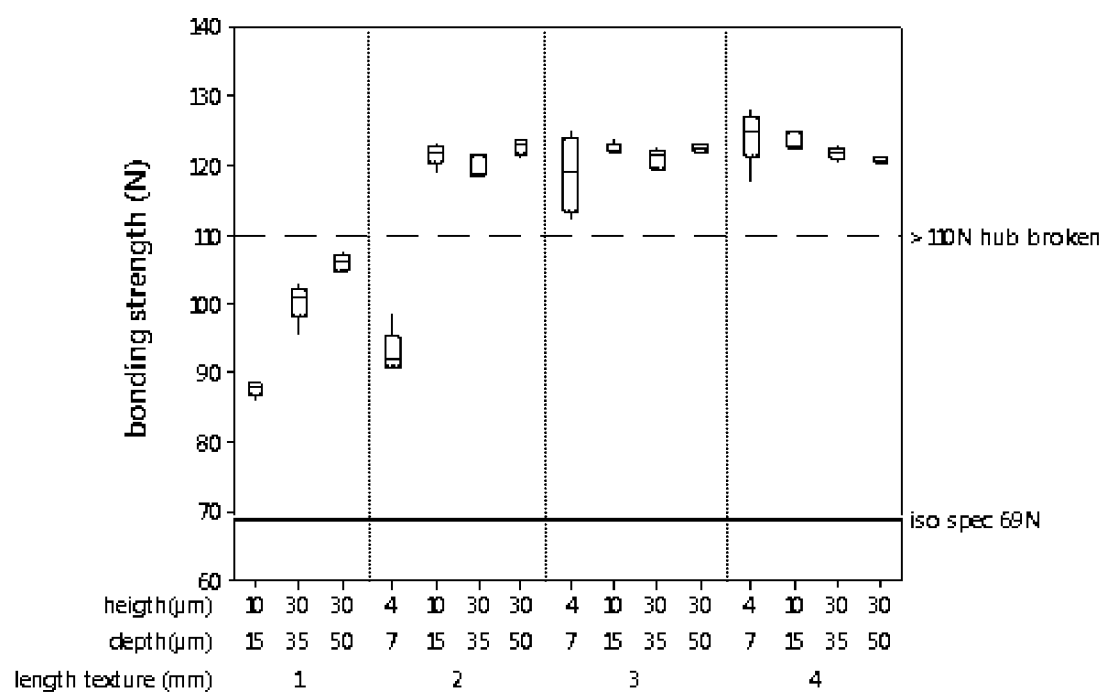
FIG. 7 represents a box plot showing the bonding strength measured on 18 G needle assemblies according to the presently disclosed subject matter.

The test results for 18 G needles are given in the box plot of FIG. 7. In this FIG. 7, the laser etched needles demonstrated a bonding strength higher than what may be required by the ISO standard, namely higher than 69 N, even the needles with the shortest textured portion length of 1 mm or with a textured portion length of 2 mm and minimum depth and height of 7 and 4 μm, respectively.

In addition, for a textured portion of at least 2 mm in length including laser etched grooves of height h of at least 10 μm and depth d of at least 15 μm, bonding strengths above 110 N are obtained. Above this value, the polymer material of the needle hub broke in the area between the area bonded to the needle and the area intended to receive the syringe tip, while the bonding between the laser etched needle and the broken polymer hub is maintained.

Because of that, textured portion lengths above 3 mm do not result in any significant improvement in terms of bonding strength, while being longer to produce by laser etching.

These test results thus illustrate the significant improvements obtained by a needle assembly of the presently disclosed subject matter.

23 G Needles

A similar test was performed with 23 G needle assemblies, using a 3 mm long textured portion and different pitches (p), depths (d) and heights (h). Twenty needle assemblies were tested for each set of pitch, depth and height.

Bonding strengths were obtained as follows:

The measured bonding strengths are well above what the ISO requirement may be for 23 G needles (34 N) and thus satisfy this standard. In addition, the polymer material of the needle hub is not broken at these values around 110 N to the contrary to the results obtained with 18 G needles. Indeed, the polymer hub is thicker for a 23 G needle than for a 18 G needle and a breaking strength of such a 23 G needle hub is around 180 N.

Based on these results a minimum textured portion length of 2.5 mm allows to reach what the ISO requirement may be for 23 G needles.

32.5 G Needles

| | Textured length | Pitch | height (μm) | | | | |
|---|---|---|---|---|---|---|---|
| | (mm) | (μm) | 17.4 | 24 | 25 | 40 | 44 |
| depth (μm) | 15 | 3 | 125 | | | 133N | |
| | 28 | 3 | 150 | | 130N | | |
| | 34.5 | 3 | 125 | 142N | | | |
| | 45 | 3 | 125 | | | 144N | 151N |
| | 50 | 3 | 100 | | | | 147N |

A similar test was performed with 32.5 G needle assemblies, using a 4 mm long textured portion, and different pitches (p), depths (d) and heights (h). Twenty needle assemblies were tested for each set of pitch, depth and height.

Bonding strengths were obtained as follows:

| | Length texture | Pitch | height (μm) | | |
|---|---|---|---|---|---|
| | (mm) | (μm) | 11 | 14.4 | 25 |
| depth (μm) | 5 | 4 | 217 | 25.5N | 35N |
| | 15 | 4 | 217 | 30N | |
| | 17.2 | 4 | 125 | | 21.9N |

These results are well above what the ISO requirement may be for 32.5 G needle (11 N) despite the tiny diameter of the 32.5 G needles (see inside and outside diameters above). Based on these results, a minimum textured portion length of 3 mm allows to reach what the ISO requirement may be for 32.5 G needles.

Summary of Optimal Parameters

Based on the above results, optimal parameters of the textured portion may be summed up as follows, depending on the needle diameter:

| Needle diameter | Optimal textured surface (mm²) | | Number of | Optimal textured length (mm) | | Pitch |
|---|---|---|---|---|---|---|
| (Gauge) | min | max | lines/mm | min | max | (μm) |
| 18 | 5.676 | 11.352 | 8 | 1 | 3 | 125 |
| 23 | 4.772 | 7.636 | 8 | 2.5 | 4 | 125 |
| 32.5 | 1.727 | 2.303 | 5 | 3 | 4 | 217 |

It is of course understood that obvious improvements and/or modifications for one skilled in the art may be implemented, still being under the scope of the presently disclosed subject matter as it is defined by the appended claims. In particular, it is referred to a hub molded over the textured portion of the needle, but alternatively, the hub might be first formed alone and in a second step coupled to the needle with a heat deformation applied to the hub over the textured portion of the needle.

In addition, the embodiments according to the present description may be mixed up in one single laser etched needle. Finally, the presently disclosed subject matter is not limited to the example needle sizes of 18 G, 23 G and 32.5 G provided above but may be applied to any size of needles, for example from 18 G to 32.5 G and beyond.

The invention claimed is:

1. A needle assembly, comprising:
a needle having a textured portion and non-textured portion adjacent to the textured portion; and
a hub arranged over at least a part of the textured portion of the needle,
wherein the textured portion includes laser etched grooves each having the same width formed on an outer surface of the needle and oriented in a circumferential direction of the needle, the laser etched grooves each being separated by a given pitch having the same length, the given pitch being lower than a predetermined length, so that protruded portions of two adjacent laser etched grooves have at least a common portion or overlap,
wherein each of the laser etched grooves has two protruded portions and a dented portion interposed between the two protruded portions so as to form an anchorage with the hub arranged over at least a part of the textured portion, the given pitch being lower than the width of a single laser etched groove and its two protruded portions, and
wherein each of the two protruded portions has a top surface located above an outer surface of non-textured portion and the dented portion has a bottom surface located below the outer surface of non-textured portion,
wherein the laser etched grooves have a minimum depth of 7 μm below the outer surface of non-textured portion and the protruded portions have a minimum height of 4 μm above the outer surface of non-textured portion, and
the laser etched grooves have a maximum depth of 50 μm below the outer surface of non-textured portion and the protruded portions have a maximum height of 44 μm above the outer surface of the non-textured portion.

2. The needle assembly according to claim 1, wherein the given pitch is chosen so that the common portion is lower than the height of the protruded portions.

3. The needle assembly according to claim 1, wherein the given pitch is chosen so that there is an indent arranged on a top portion between two protruded portions having at least a common portion or overlap.

4. The needle assembly according to claim 1, wherein the laser etched grooves have a minimum depth of 10 μm below the outer surface of non-textured portion for a needle having a textured area covered by the hub of at least 3 mm length along the needle axial direction.

5. The needle assembly according to claim 1, wherein the dented portion of the laser etched grooves has a minimum depth, wherein the needle presents a wall thickness, and wherein the minimum depth is chosen in the range from 10% to 50% of the wall thickness.

6. The needle assembly according to claim 1, wherein the protruded portions have a minimum height of 10 μm above the outer surface of non-textured portion.

7. The needle assembly according to claim 1, wherein the pitch is 125 μm±40 μm.

8. The needle assembly according to claim 1, wherein the hub is molded over the needle, or is heat-deformed over the needle, and is manufactured with a material chosen from polymers, and containing at least one of polyethylene, polypropylene, or cyclic polyolefin.

9. The needle assembly according to claim 1, wherein the laser etched grooves extend in the circumferential direction along 360°.

10. The needle assembly according to claim 1, wherein the laser etched grooves extend in the circumferential direction along about or less than 180°.

11. The needle assembly according to claim 1, wherein the laser etched grooves are shifted between two opposite sides of the needle.

12. The needle assembly according to claim 1, wherein the hub is molded over the entire textured portion.

13. A syringe for use with a liquid and a patient, comprising:
the needle assembly according to claim 1,
wherein the syringe is configured for injecting the liquid into the patient.

* * * * *